United States Patent [19]

Foglia et al.

[11] 4,371,469

[45] Feb. 1, 1983

[54] PROCESS FOR THE PREPARATION OF BRANCHED CHAIN FATTY ACIDS AND ESTERS

[75] Inventors: Thomas A. Foglia, Lafayette Hill; Theodore Perlstein; Yoshio Nakano, both of Philadelphia; Gerhard Maerker, Oreland, all of Pa.

[73] Assignee: The United States of America as represented by the Secretary of Agriculture, Washington, D.C.

[21] Appl. No.: 258,482

[22] Filed: Apr. 28, 1981

[51] Int. Cl.$^3$ .............................................. C09F 7/08
[52] U.S. Cl. ................................ 260/405.6; 260/407; 260/413
[58] Field of Search .............. 260/405.6, 407, 413 R, 260/419

[56] References Cited

U.S. PATENT DOCUMENTS

| | | | |
|---|---|---|---|
| 2,482,761 | 9/1949 | Goebel | 260/407 |
| 2,793,220 | 6/1957 | Barrett et al. | 260/407 |
| 2,812,342 | 7/1957 | Peters | 260/409 |
| 3,632,822 | 1/1972 | Conroy | 260/407 |

OTHER PUBLICATIONS

Foglia et al. JAOCS 57 No. 2 Feb. 1980, (Abst. No. 368).
Goebel, JAOCS 24, 65–68, 1947.
McMahon et al., JAOCS 51, 522–527, 1974.
Eisner et al., JAOCS 51, 381–384, 1974.

*Primary Examiner*—John F. Niebling
*Attorney, Agent, or Firm*—M. Howard Silverstein; William E. Scott; David G. McConnell

[57] ABSTRACT

Complex mixtures of branched chain fatty acids or esters in which the yield of monomeric branched chain products are substantially increased and the yield of polymeric products substantially decreased are prepared by heating monounsaturated fatty acids or esters in the presence of certain combinations of catalysts.

11 Claims, No Drawings

PROCESS FOR THE PREPARATION OF BRANCHED CHAIN FATTY ACIDS AND ESTERS

BACKGROUND OF THE INVENTION

1. Field of the Invention

This invention relates to an improved process for the preparation of complex mixtures of branched chain fatty acids or esters and more particularly, to methods for substantially increasing the amounts of monomeric branched products and decreasing the amounts of polymeric products when monounsaturated fatty acids or esters are heated in the presence of certain combinations of catalysts.

2. Description of the Art

It is known in the art that dimer and polymerized fatty materials may be prepared either from unsaturated fatty acids or fatty acid esters by heating them with or without a clay catalyst. The starting fatty acids or esters employed in these polymerization reactions have been described as being either monounsaturated or polyunsaturated fatty materials. In the prior art the main objective has usually been the production of dibasic or dimerized fatty acids or esters.

In the course of preparing polymerized fatty acids it is customary to separate the dibasic or dimerized fatty acids from unpolymerized fatty acids, usually by distillation. These unpolymerized fatty acids are referred to as the monomeric fraction. In effecting the polymerization of unsaturated fatty acids or esters, a secondary reaction occurs concurrently, which results in a structural modification of a portion of the monomeric unsaturated fatty acid or ester. Such structural modification of the starting fatty material does not permit further polymerization. The structurally modified or isomerized fatty acids are formed to a greater or lesser degree as co-products of all thermal methods of polymerizing unsaturated fatty acids either in the presence or absence of a natural clay catalyst. A number of modifications of the dimerization reaction of unsaturated fatty acids and esters have been reported in the prior art, all with the intention of improving the conversion of starting fatty acids to the dibasic or dimer fatty acids. The most widely practiced modification of the process is to employ water in the polymerization process to suppress decarboxylation leading to hydrocarbon products. The most widely used catalysts, are the natural crystalline clays such as the montmorillonites.

It is also known in the art that use of 1,2-dichloroethane as a co-catalyst with an acid clay catalyst increased somewhat the yield of branched chain acids over that obtained with only the clay catalyst.

Under the most favorable conditions employed for the dimerization or polymerization of unsaturated fatty acids a portion of the starting fatty acid does not polymerize. This unpolymerized material is typically separated from the polymerized acids by distillation and is commonly referred to as the monomeric fraction. This monomeric fraction is known to contain saturated fatty acids originally present in the starting material or formed in the course of the polymerization reaction, structurally modified or branched chain fatty acids and unchanged or only slightly modified unsaturated fatty acids. The structurally modified or branched chain fatty acids are not shorter chain fatty acids produced by cracking, are in the $C_{16}$–$C_{18}$ range and retain most of the original unsaturation of the starting fatty acids. The branched chain acids are usually separated from the unmodified fatty acids by hydrogenation to saturated fatty acids followed by low temperature crystallization which removes the normal chain fatty acids. In most instances the amount of branched fatty acids produced does not exceed the amount of the dimeric fatty acids formed and typically they are formed in minor amounts.

SUMMARY OF THE INVENTION

An object of this invention is to provide a process for the preparation of complex mixtures of branched chain fatty acids or esters.

Another object is to provide a process for preparing complex mixtures of branched chain fatty acids or esters in which the yield of monomeric branched chain acids or esters is substantially increased while the yield of polymeric products is substantially reduced.

The above and other objects are accomplished by a process wherein a predominantly monounsaturated fatty acid or ester or mixture thereof are heated at increased pressures in the presence of an acid catalyst and two co-catalysts until the reaction is complete, the reaction mixture cooled, gaseous products vented off, the catalysts removed, the reaction mixture distilled to separate the polymeric products from the monomeric products, and the branched chain monomeric products separated from the unbranched chain monomeric products. One of the two co-catalysts is a protonic acid or an organic compound from which a protonic acid may be generated in situ during the reaction. The other co-catalyst is a saturated volatile hydrocarbon having a chain length of from two to nine carbon atoms.

DESCRIPTION OF THE INVENTION

The mixtures of randomly branched fatty acids and esters formed by the process of this invention possess important physical properties that make their use attractive to the lubricant and cosmetic industries. The products, when saturated by hydrogenation, are liquid at room temperature and below and combine the high fluidity and lubricity normally found in esters of mono and polyunsaturated unbranched fatty acids with the excellent thermal and oxidative stability normally associated with esters of saturated, unbranched fatty acids.

Mixtures of branched fatty acids and esters such as are produced by the process of this invention are items of commerce and find application in industrial lubricating oils and greases and in cosmetic preparations. Because of their excellent physical properties they are much in demand, but they are in short supply, since their only current source of supply is as a by-product of the industrial manufacture of dimer acids. In current industrial practice of dimer acid manufacture the branched products appear in admixture with unreacted, recovered starting materials, and hence their volume of supply is controlled and limited by the amount of dimer acid produced.

The process of this invention overcomes the disadvantage of having the supply of branched products limited by the demand for dimer acids and permits the production of the branched product by an independent procedure and as the predominant reaction product.

The process of this invention consists of heating a predominently monounsaturated fatty acid or its ester in a pressure vessel in the presence of an acid catalyst and two co-catalysts. We discovered that the use of two co-catalysts, each selected from a different group of chemicals hereafter described, greatly increases the yield of desired branched chain fatty acids or esters. In addition, we also discovered that the second co-catalyst suppresses the cracking of the fatty acids to lower chain homologs thereby contributing to a further increase in the yield of branched chain fatty acids or esters and that it improves the color of these products. At the end of the chosen reaction period the mixture is cooled, the catalysts, if solid, are removed by filtration, and the reaction mixture is subjected to a residue-freeing distillation to remove any polymeric by-products. If one or more of the catalysts is a liquid, it is separated by procedures well-known in the art. The distillate, which may be a mixture of acids or of mixed acids and esters, may be used without further treatment or it may be subjected to a further procedure in which the branched products are separated from unbranched materials.

The starting materials for the process of this invention may be any predominantly monounsaturated fatty acids of animal or vegetable origin or their esters with low molecular weight alcohols. The acids or esters may be in the form in which they are obtained from animal or vegetable oils by transesterification or other suitable means, or they may be purified prior to use by removal of unsaponifiable materials, pigments or other impurities, saturated fatty acids or esters, or other natural components of such fats and oils.

Catalysts that are effective in the process of this invention are Lewis acids and acid clays. The Lewis acids that are most effective are salts such as aluminum chloride and bromide, boron trifluoride, iron and tin salts and others. Preferred are natural clays, the aqueous suspensions of which have a pH of less than 7. For best results the aqueous suspension of clay catalyst should have a pH in the range of 3 to 5. Natural clays that have these desirable properties are the bentonites, but any clay mineral within the pH range specified above may be used. The amount of clay catalyst used in the reaction is in the range of 3 to 20%, and preferably from 5 to 10 weight percent based on the weight of the starting acid or ester.

In order to attain the objectives of the invention and maximize the yield of the desired branched chain acids or esters, two co-catalysts must be used. One of the co-catalysts that have been found to be effective in the process of this invention is chosen from a group of chemicals including protonic acids such as hydrochloric acid, sulfuric acid, sulfonic acid and phosphoric acid and organic compounds from which such protonic acids may be generated in situ during the reaction and which act also as diluents. Examples of such organic compounds are 1,2-dichloroethane, 1,2-dichloropropane, alcohol sulfates, and alcohol phosphates. Ordinarily, the amount of diluent acid generator is in the range of 100 to 300 weight percent based on the weight of the starting material, while the amount of protonic acid used directly ranges from 0.5 to 8 weight percent based on the weight of the starting material.

The second co-catalyst which is employed in the process of this invention is chosen from a group of chemicals including saturated volatile hydrocarbons of $C_2$ to $C_9$ chain length. In addition to providing improved yields of branched fatty acids, these co-catalysts suppress the cracking of the fatty acids to lower chain homologues, thereby increasing the yield of modified acids. These co-catalysts also improve the color of the final monomeric branched chain product. Examples of this type of co-catalyst are isobutane, isopentane, isohexane, and 2,3-dimethylbutane.

Branched hydrocarbons may also be used as the second co-catalyst and have been found to effectively promote branched fatty acid or ester production, improve the properties of the products and decrease competing chain cleavage reactions. Typically, the amount of branched hydrocarbon that may be used is in the range of 50-80 weight percent based on the amount of starting material. Isobutane is an example of this type of co-catalyst.

Best results are obtained when the reaction is carried out at a temperature of 200°-250° C., at elevated pressures and at times ranging from one to twenty-four hours depending on the catalyst system employed. It is not necessary to dehydrate reagents, starting materials or equipment, but best product yields are obtained when the amount of added water is kept to a minimum.

Upon completion of the reaction period, the reaction mixture is allowed to cool and gaseous products are removed by venting. The catalysts are removed and the reaction mixture is then subjected to a residue-freeing distillation to separate the desired monomeric materials from polymeric products. The monomeric products, which typically consist of mixtures of branched and straight chain saturated and unsaturated acids or acids and esters, may be treated by any of a large variety of methods known to the art depending on the final product desired. For example, the mixture may be esterified by commonly employed procedures to produce a mixture of esters, or it may be hydrogenated to produce a mixture of branched and straight chain saturated acids or esters in which the straight chain products can be separated from the branched materials by cooling, or the straight chain materials can be separated from branched materials by urea complexing processes that are well known.

The invention is illustrated as follows. Examples 1 and 2 in which no co-catalyst and one co-catalyst, respectively, is used, are described for purposes of comparison with the process of this invention as exemplified in Examples 3 and 4.

EXAMPLE 1

One hundred grams of laboratory grade methyl oleate (98% C18:1, 2% C18:0) and 5 grams of clay catalyst (bentonite) were placed into an autoclave under 30 p.s.i. of nitrogen. The autoclave was heated to a temperature of 250° C. for 24 hours to a maximum pressure of 200 p.s.i. After cooling, the mixture of polymerized and unpolymerized esters was filtered and distilled under vacuum. The polymerized esters, 30 grams, remained in the still as a residue, and 62 grams of monomeric distillate was obtained. The distillate was taken up in methanol (600 ml) and urea, 90 grams, added. The mixture was heated until complete solution was obtained and then cooled to room temperature and the crystallized urea removed by filtration. The filtrate was diluted with water (1500 ml) and extracted with hexane (3×200 ml). The hexane extracts were combined and the solvent removed under a reduced pressure of about 0.05 mm to give 29 grams of branched chain fatty esters, Iodine Value 72.5. The urea crystals were dissolved in water (500 ml) and the aqueous solution extracted with hexane (3×200 ml). The extracts were combined and the solvent removed in vacuo to give 33 grams of normal chain fatty methyl esters, Iodine Value (IV) of 70. Gas-liquid chromatography (GLC) showed the chain length of the branched chain esters to be predominantly $C_{18}$.

EXAMPLE 2

One hundred grams of 98% oleic acid were heated in an autoclave at 220° C. for 3 hours in the presence of 10 grams of clay (bentonite) and 200 grams of 1,2-dichloroethane. The maximum pressure reached during the course of the reaction was 500 p.s.i. The product mixture was filtered and the 1,2-dichloroethane removed under reduced pressure. Distillation of the product mixture under a reduced pressure at about 0.05 mm gave 60 grams of monomer distillate and 40 grams of polymeric acids as a residue. The monomeric distillate was separated by urea adduction into branched chain acid portion, 35 grams, saturated and unsaturated fatty acid portion, 13 grams, γ-stearolactone, 6 grams and an unidentified product, 6 grams. The branched chain acids were $C_{18}$ by GLC.

EXAMPLE 3

One hundred grams of 98% methyl oleate was heated in an autoclave to 230° C. for 2 hours in the presence of 10 grams of clay (bentonite), 60 grams of isobutane and 200 grams of 1,2-dichloroethane. The maximum pressure reached during the reaction was 880 p.s.i. After cooling, the autoclave was vented, the clay catalyst removed by filtration and the excess 1,2-dichloroethane removed under a reduced pressure of about 0.05 mm. Distillation of the reaction product gave 29 grams of polymeric residue and 65 grams of monomeric distillate. The monomer fraction (IV, 62) was hydrogenated with Adam's catalyst ($PtO_2$) until the IV had decreased to 24. The monomer fraction was then taken up in acetone, cooled to 2° C., and the precipitated solid straight chain esters, 6 grams, removed by filtration. The liquid branched chain esters were recovered by evaporation of the solvent and amounted to 59 grams having an iodine value of 34. GLC showed the chain length of the esters to be $C_{18}$.

EXAMPLE 4

One hundred grams of 98% oleic acid were heated in an autoclave at 220° C. for 3 hours in the presence of 10 grams of clay (bentonite), 70 grams of isobutane and 200 grams of 1,2-dichloroethane. Maximum pressure reached was 700 p.s.i. The autoclave was cooled, the isobutane released, catalyst removed by filtration, and the 1,2-dichloroethane removed at a reduced pressure of about 0.05 mm. The crude product mixture was distilled to give 69 grams of distillate and 31 grams of polymerized acids. The monomeric distillate was fractionated by urea adduction to give 53 grams of branched chain fatty acids, 8 grams of straight chain fatty acids and 8 grams of γ-stearolactone. GLC of the straight chain fraction showed it to be mostly saturated. The branched chain acids were $C_{18}$ by GLC.

We claim:

1. In a process for the preparation of complex mixtures of branched chain fatty acids or esters wherein monounsaturated fatty acids or esters or mixtures thereof are heated in the presence of a catalyst, the steps by which the yield of monomeric branched chain products is substantially increased and the yield of polymeric products is substantially decreased, comprising:
   (a) heating a predominantly monounsaturated fatty acid or ester or mixture thereof at increased pressure in the presence of an acid catalyst and two co-catalysts until the reaction is completed;
   (b) cooling the reaction mixture;
   (c) venting off gaseous products;
   (d) removing the catalyst;
   (e) distilling the reaction mixture to separate polymeric by-products; and
   (f) separating the branched chain products from the unbranched chain products.

2. In a process for the preparation of complex mixtures of branched chain fatty acids or esters wherein monounsaturated fatty acids are heated in the presence of a catalyst, the steps by which the amount of monomeric branched chain products is substantially increased and the amount of polymeric products is substantially decreased, comprising:
   (a) heating a material selected from the group consisting of fatty acids and mixtures thereof, fatty acid esters and mixtures thereof, and mixtures of fatty acids and fatty acid esters, said acids and esters being predominantly monounsaturated, at increased pressure in the presence of a catalyst selected from the group consisting of Lewis acids and clay acids, and also in the presence of two co-catalysts, one of which is selected from the group consisting of protonic acids and organic compounds from which protonic acids may be generated in situ during the reaction and one of which is selected from the group consisting of saturated volatile hydrocarbons having a chain length of from two to nine carbon atoms, said heating being continued until the reaction is complete;
   (b) cooling the reaction mixture and venting off any gaseous products;
   (c) removing the catalyst;
   (d) distilling the reaction mixture to separate polymeric by-products; and
   (e) separating the branched chain products from the unbranched chain products.

3. The process of claim 2 in which the predominantly monounsaturated ester is methyl oleate.

4. The process of claim 2 in which the predominantly monounsaturated acid is oleic acid.

5. The process of claim 2 in which the predominantly monounsaturated material is a mixture of methyl oleate and methyl stearate.

6. The process of claim 2 in which the predominantly monounsaturated acids and esters are derived from animal oils.

7. The process of claim 2 in which the predominantly monounsaturated acids and esters are derived from vegetable oils.

8. The process of claim 2 in which a co-catalyst is a protonic acid selected for the group consisting of hydrochloric acid, sulfuric acid, sulfonic acid and phosphoric acid.

9. The process of claim 2 in which a co-catalyst is an organic compound selected from the group consisting of 1,2-dichloroethane, 1,2-dichloropropane, alcohol sulfates and alcohol phosphates.

10. The process of claim 2 in which a co-catalyst is a saturated volatile hydrocarbon selected from the group consisting of isobutane, isopentane, isohexane and 2,3-dimethylbutane.

11. The process of claim 2 in which the predominantly monounsaturated fatty material is heated at a temperature of about 220° to 230° C. for up to 3 hours at a pressure of up to 880 p.s.i. in the presence of bentonite, 1,2-dichloroethane and isobutane.

* * * * *